United States Patent [19]

Reinhartz

[11] Patent Number: 4,774,173

[45] Date of Patent: Sep. 27, 1988

[54] MICROBIOLOGICAL ASSAY KIT AND METHOD FOR DETECTING DE NOVO BIOMOLECULAR SYNTHESIS INHIBITORS

[75] Inventor: Avraham Reinhartz, Sireny, Israel

[73] Assignee: Orgenics Ltd., Yavne, Israel

[21] Appl. No.: 679,077

[22] Filed: Dec. 6, 1984

[51] Int. Cl.$^4$ .......................... C12Q 1/70; C12Q 1/02; C12Q 1/18

[52] U.S. Cl. ......................................... 435/5; 435/29; 435/32; 435/810

[58] Field of Search ..................... 435/4, 5, 14, 18, 29, 435/32, 253, 849, 810; 436/63; 424/9; 935/43

[56] References Cited

U.S. PATENT DOCUMENTS

| | | | |
|---|---|---|---|
| 2,967,132 | 1/1961 | Sacks | 435/32 X |
| 4,073,694 | 2/1978 | Buda et al. | 435/32 X |
| 4,104,126 | 8/1978 | Young | 435/5 |
| 4,239,852 | 12/1980 | Charm | 435/32 |
| 4,464,471 | 8/1984 | Armentrout et al. | 435/253 |

OTHER PUBLICATIONS

Kornberg, DNA Replication, 1980, W. H. Freeman and Co. San Francisco, p. 41.
Maniatis et al., Molecular Cloning a Laboratory Manual, Cold Springs Harbor Laboratory, (1982), p. 31.
Choi et al., Biochem. Biophysics Res. Comm., 94:755–762, 1980.
Blattner et al., 1977, Science, 196:161.
Casadaban, M. J. et al., J. Bacteriol., 143:971–980, 1980.
Sinsky and Silverman, J. Bacteriol., 101:429–437, 1970.
Rubenstein et al., J. Bacteriol., 104:443–452, 1970.
Kohsaka and Demain, 1976, Biochem. Biophys. Res. Comm. 70:465–473.
Scheie, J. Bacteriol. 98:335–340, 1969.
Scheie and Rehberg, J. Bacteriol. 109:229–235, 1972.
Sedgwick and MacLeod, Cam. J. Biochem. 58:1206–1214, 1980.
Rhoads and Epstein, J. Biol. Chem. 252:1394–1401, 1977.
"Bacterial Toxins" in Aspects of Microbiology 2, pp. 78–80, J. Stephen and R. A. Pietrowski, American Society for Microbiology.

Primary Examiner—Robert J. Warden
Assistant Examiner—Randall E. Deck
Attorney, Agent, or Firm—Sandler & Greenblum

[57] ABSTRACT

A method for assaying a specimen for the presence of a substance capable of inhibiting de novo biomolecular synthesis in a test microorganism, which comprises: exposing a cell wall permeability-enhanced test microorganism exhibiting delayed de novo synthesis of said biomolecule to said specimen, and assaying the extent of inhibition of synthesis of said biomolecule in said microorganism. A kit is described for performing the method, as well as a reaction mixture for performing the technique.

14 Claims, No Drawings

MICROBIOLOGICAL ASSAY KIT AND METHOD FOR DETECTING DE NOVO BIOMOLECULAR SYNTHESIS INHIBITORS

BACKGROUND OF THE INVENTION

1. Field of the Invention

This invention relates to an assay kit and method for detecting the presence and extent of substances capable of inhibiting de novo biomolecular synthesis, such as toxicants, and antibiotics.

2. Description of Background and Relevant Information

Conventional toxicity bioassays using animals or animal cells are time consuming and expensive to perform. Of short term bioassays which are presently known, bacterial tests are the most suitable for screening chemical toxicity because they are easy to perform, reproducible and not expensive. Existing microbial tests measure growth inhibition, oxygen uptake, luminescence, colony-forming ability, ATP content and enzymatic activity.

Field-oriented assays are needed which are quick, sensitive and simple, for detection of toxicants in water, chemicals, pharmaceuticals, cosmetics, foodstuffs and food additives. By way of example, field testing is essential in antibiotic testing in milk, and in sera and urine.

A number of bacterial toxicity screening systems in use include a bioluminescence test (Microtox test of Beckman) based on the principle of light reduction upon exposure to toxicants (QURESHI et al., Article entitled Evaluation and Refinement of the Microtox Test for use in Toxicity Screening in "Toxicity Screening using Procedures Bacterial Systems", edited by Liu et al., National Water Research Institute, Burlington, Ontario, Canada 1984, pp. 1-2; the Spirillum volutans test for use in toxicity screening (GOATCHER et al., Article entitled Evaluation and Refinement of the Sprillum Volutans Test for Use in Toxicity Screening, in Toxicity Screening, Supra., pp. 89-108, 1984 and the tetrazolium reduction assay (KOOPMAN et al., Article entitled Validity of Tetrazolium Reduction Assays for Assessing Toxic Inhibition of Filamentous Bacteria in Activated Sludge, in Toxicity Screening, Supra., pp. 147-162, 1984.

The first system is quite sensitive but requires expensive instrumentation. The other methods are complicated to perform or lack the proper sensitivity required for toxicant analysis in water and foodstuffs. The literature discloses additional techniques in which relatively rapid and sensitive assaying is possible based upon observation of protein synthesis inhibition.

By way of example, streptomycin has been found to inhibit de novo protein synthesis, and to only partially inhibit ongoing (translational) protein synthesis (ZIERBUT et al. Eur. J. Biochem. 98: 577-583, 1979; DAVIS et al., Article entitled: "Complex Interaction of Antibiotics with the Ribosomes" in "Ribosomes" edited by Nomura et al., Cold Spring Harbor Laboratory, pp. 755-762, 1974; CHOI et al., Biochem. Biophysics Res. Comm. 94: 755-762 1980 ARTMAN et al., Antimicrob. Agents Chemother. 7: 449-455, 1972. Utilizing the inhibition or protein synthesis, it is possible to assay for the presence of a toxicant or the like. However, such a technique has been possible only with toxicants and the like which are fast acting, and which rapidly inhibit de novo protein synthesis. Where a toxicant is slow acting, it could not be assayed using this technique because there is insufficient inhibition before translational synthesis begins.

It would, therefore, be desirable if such techniques could be improved in a way which would also permit the assaying of substances which inhibit de novo protein synthesis, but which are slower acting.

There is thus a demand for a rapid, field-oriented kit with high sensitivity, whose procedures are simple to perform and which gives visibly detectable results, even with substances which themselves only relatively slowly inhibit de novo protein synthesis.

SUMMARY OF THE INVENTION

It is thus an object of the invention to provide an assay which satisfies the various criteria recited above. The present invention achieves the stated objectives by providing a simple, rapid (1-2.5 hours) assay, e.g., colorimetric, which does not require special equipment and which can easily be performed under field conditions.

According to one aspect of the invention, a method is provided for assaying the presence of substances which inhibit de novo biomolecular synthesis, such as toxicants, e.g. antibiotics, in a specimen by exposing an organism to a biomolecule-inducing agent in the presence of the specimen, and assaying the extent of inhibition of the synthesis of such biomolecule, as by the use of an indicator. In one embodiment the biomolecule is preferably an enzyme; and the test organism is a stressed recovering microorganism, preferably a bacterium. When the biomolecule is an enzyme, a chromogenic substrate is utilized whereby the extent of color change is a measure of the inhibition of enzyme synthesis.

In order to improve the sensitivity of the assay, the organism is most preferably a stressed polysaccharide-deficient strain of Escherichia coli, e.g., ESS. This bacterium synthesizes beta-galactosidase as a result of inducement by a specific enzyme inducer, such as lactose or isopropyl beta-D-thiogalactopyranoside (IPTG).

The specific inducer is preferably employed in a mixture which also contains factors required for the recovery of the E. coli bacteria from the stress. For example, potassium chloride admixed with proline or monosodium glutamate assists in stress recovery, while the mixture may additionally comprise a high concentration of sodium chloride as a stress-inducing agent.

The amount of enzyme produced by the bacteria is assayed by adding a chromogenic substrate sensitive to the enzyme and measuring the color change, for example, by colorimetric or optical density techniques.

Rather than specifically employing a stress inducing agent in the mixture, the external conditions or physical characteristics of the bacteria itself may be utilized to induce stress. Thus, by using lyophilized bacteria which have been re-suspended in the mixture containing the toxicant, the recovery from the lyophilized state creates the stress condition. The resulting mixture may be incubated in a growth medium to obtain a test culture and the extent of the color change in the culture is assayed after further incubation.

According to another embodiment of the invention, rather than relying upon an inducer, lyophilized bacteria is infected with a bacteriophage, which upon rehydration is induced to express an enzyme. Expression occurs to a lesser extent, or is prevented, in the presence of toxicants. For example, the phage Charon 4A (Blattner et al., 1977, Science 196: 161), contains beta-galactosidase gene which is expressed in *E. coli* upon infection with the phage. This expression may be inhibited by toxicants.

According to a further embodiment of the invention in which the sensitivity of the system is increased, other extra chromosomal coding elements are introduced into the cell. For example, plasmids containing the chromogenic enzyme code are introduced into a cell to produce a chromogenic enzyme like beta-galactosidase (Casadaban, M. J. et al, J. Bacteriol., 143: 971–980, 1980). Since now a considerable quantity of beta-galactosidase has been produced, less cells can be used in the test and thus the sensitivity of the system is increased. Cells recovering from a stress e.g. lyophilization) now applied produce further beta-galactosidase. This further production occurs to a lesser extent, or is prevented, in the presence of toxicants. In a particular example, plasmid pMC874, when introduced into bacterial cells, produces the enzyme beta-galactosidase (Casadaban, M. J. et al, J. Bacteriol, 143: 971–980, 1980). Cells recovering from a stress (e.g. lyophilization) now applied produce further beta-galactosidase. This further production may be inhibited by toxicants.

Where the toxicant or antibiotic is one which acts only on the cell wall, an auxiliary or "messenger" toxicant, whose toxicity is limited by its inability to penetrate the cell wall, is admixed with the mixture along with the specimen. The "messenger" is capable of inhibiting de novo protein synthesis as a function of the extent to which it is capable of penetrating the cell. This is a function of the potency of the toxicant.

Another aspect of the invention involves a kit for use in performing the assay procedure. This kit includes, in separate containers, (a) a test microorganism which has been prestressed, or which is to be stressed; (b) a biomolecule inducing agent; and (c) a component enabling recovery of the microorganism from stress.

The microorganism may preferably be a lyophilized polysaccharide-deficient strain of *E. coli*, and a growth medium may also be provided. Where the microorganism has not been prestressed, an agent to stress the microorganism is also provided, e.g. a high sodium chloride concentration.

The component for enabling recovery of the biomolecule from the stress may be, e.g., potassium chloride and proline or monosodium glutamate.

An inducer for beta-galactosidase, e.g. beta-D-thiogalactopyranoside or lactose, is particularly preferred. Alternatively, or in addition, an inducer for beta-galactosidase may be utilized. The kit may additionally include an indicator to indicate toxicity as a function of inhibition.

The kit may also contain a stop solution; and a standard microtitration plate.

DETAILED DESCRIPTION OF THE INVENTION

The assay is based on the property of certain substances such as toxicants and antibiotics of inhibiting de novo synthesis (as opposed to ongoing synthesis) of biomolecules in microorganisms. It is with such substances that the technique of the invention finds particular application.

As opposed to prior techniques, the technique of the invention makes it possible to assay for the presence of even slow-acting inhibitors of de novo protein synthesis. This is achieved by contacting the sample with a microorganism such as a bacteria which has been stressed and then allowed to recover. It is during the recovery period that de novo protein synthesis is delayed to an extent sufficient to allow the toxicant or the like to act and inhibit de novo protein synthesis.

One technique of stressing microorganisms to achieve the desired effect is to lyophilize them. SINSKY and SILVERMAN, J. Bacteriol. 101: 429–437, 1970, have shown that after lyophilization of *Escherichia coli* cells, a recovery period (incubation in nutrient medium) of about 30 minutes is required before the capacity to snythesize beta-galactosidase is reestablished. They have also shown that immediately after rehydration the permeability of these cells to antibiotics dramatically increases.

Stress can alternatively, or additionally be produced by plasmolysis (CHARLANG and HOROWITZ, J. Bacteriol. 117: 261–264, 1974; MUNRO et al., J. Bio. Chem. 247: 1272–1280, 1972; BATTERSON and VAN BAALEN, Arch. Mikrobiol. Z., 76: 151–165, 1971; RUBENSTEIN et al., J. Bacteriol. 104: 443–452, 1970); or heat shock (HURST, Can. J. Microbiol 23: 935–944, 1977).

The recovery process from freeze drying or from plasmolysis requires energy and active transport (MEASURES, Nature 257: 398–400, 1975; EPSTEIN and LAIMINS, TIBS, 1980; HAROLD and ALTENDORF, Current Topics in Membranes and Transport, Vol. 5: 1–50, 1974; SEDGWICK and MACLEOD, Can. J. Biochem. 58: 1206–1214, 1980; RHOADS and EPSTEIN, J. Biol. Chem. 252: 1394–1401, 1977). For this reason, the invention preferably contemplates the presence of a growth medium and of a transport salt such as potassium chloride in admixture with the test microorganism.

By way of illustration, the inventive technique may be applied to toxicants such as cyanide (SEDGWICK and MACLEOD, Can. J. Biochem., Ibid) and phenol (KROLL and ANAGNOSTOPOULOS, J. App. Bacteriol. 51: 313–323, 1981), which completely inhibit recovery and, therefore, prevent the de novo synthesis of proteins.

When the test microorganism is a rough mutant (a mutant possessing a deficient outer membrane, e.g., a polysaccharide-deficient strain), the sensitivity of the assay is increased due to the increased permeability of the bacterial cell wall. For example, a rough mutant of *Escherichia coli* referred to as *E. coli* ESS, which was developed by Kohaka and Demain, 1976, Biochem. Biophys. Res. Comm. 70: 465–473, which is highly sensitive to a wide spectrum of toxic substances, such as pesticides, mycotoxins and heavy metals is preferably employed according to the invention, because of its increased sensitivity.

As was noted above, the assay is performed under stress conditions in a one step reaction in a mixture containing all the necessary elements. Stress conditions may include, but are not restricted to: osmotic pressure, differential across the cell wall, i.e., high or low external osmotic pressure, temperature shock (heat or cold), unfavorable pH, radiation, differential ion concentration, presence of other bacteria or molds, presence of certain chemical compositions etc.

Thus, as used throughout the specification and claims, the "stress" is a stimulus which, when applied to the cell of the microorganism, causes the cell metabolism and the integrity of the cell to change. the stress conditions are ameliorated or improved, the cell recovers during a recovery period in which metabolic rate increases, to allow for cell repair and restoration. During this period of heightened cell metabolism, the cell is particularly sensitive to intoxication which interferes with the metabolic activities involved in the recovery process of the cell.

The invention relates as well to the one-step assay mixture which contains the toxicant or antibiotic, the bacteria, high sodium chloride concentration on the order of about 15-25% to cause stress conditions, essential factors for bacterial recovery (potassium chloride and proline or glutamate) and a specific inducer for beta-galactosidase, e.g., isopropyl beta-D-thiogalactopyranoside (IPTG) or lactose.

In such one-step assays, sequential events occur. First, the bacteria undergoes plasmolysis which is known to increase cell wall permeability and cause a sharp decrease in all metabolic activities (SCHEIE, J. Bacteriol. 98: 335-340, 1969, SCHEIE and REHDERG, J. Bacteriol. 103: 223-225, 1972). This stage is followed by progressive deplasmolysis, that requires, in particular, active transport across the membrane, respiration and energy metabolism (DHAVISES and ANAGNOSTOPOULOS, Microbios. Letters. 7: 149-159, 1978).

By stressing the test microorganism using the assay procedure of the invention four main advantages are achieved:

1. Increase in permeability during plasmolysis which increases sensitivity of the system towards otherwise non-penetrating toxicants.

2. Increase in the number of physiological functions essential for enzyme induction. All, or any one, of these functions may be sensitive to inhibition by the toxicants or antibiotics, thereby enlarging the spectrum of toxicant or antibiotic targets.

3. Separation of the period of toxicant activity from the maximum rate of induction of beta-galactosidase (occurring at the end of deplasmolysis) which enables a maximal toxic effect prior to induction in a one-step procedure.

4. The process of induction of de novo protein synthesis is sensitive to toxicants and antibiotics because energy as well as RNA and protein synthesis are involved.

To increase the sensitivity of the assay and to allow for the assay of toxicants and antibiotics which act only on the outer membrane (cell wall), a modified strategy may be employed. In this approach, the assay mixture contains threshold levels of an auxiliary or "messenger" toxicant, e.g., gentian violet or actinomycin D, the toxicity of which is limited by its inability to penetrate the cell wall. Any cell wall permeability increase occurring as a result of the analyzed substance influencing the cell wall permeability will enable the "messenger" toxicant to enter and inhibit enzyme induction. Thus, according to the invention, a messenger toxicant may be used both to increase sensitivity to toxicants generally, as well as to allow for the assay of substances which only affect cell wall permeability.

To summarize, the principle of the invention is based on exposing recovering stressed bacteria to such conditions that cell permeability and sensitivity toward a wide spectrum of toxicants and antibiotics are enhanced. Thus, the cell is forced to operate at maximal metabolic effort to recover from the stress, and the toxin action is separated from induction by a biological delay mechanism (plasmolysis-deplasmolysis).

In the assay, serial dilutions of the sample are mixed with the stressed bacteria and a mixture containing the specific inducer for the chromogenic enzyme and essential factors required for the recovery of the bacteria from their stressed condition. The ability of cells to synthesize enzymes under these conditions depends on their ability to recover from the stress (SINSKY and SILVERMAN, J. Bacteriol. 101: 429-437, 1970). Toxic materials interfere with and/or inhibit the recovery process and with it the synthesis of beta-galactosidase.

The amount of the de novo synthesized enzyme may be determined by a pronounced colorimetric reaction. It is particularly advantageous to monitor the de novo synthesis of an enzyme, using a chromogenic substrate, because of the ease of detecting such a biomolecule.

The assay procedure of the invention readily lends itself to containerization in a kit which is field-oriented and easy to operate. By way of example, the kit may contain the bacteria in a lyophilized form and all the reagents are stabilized so that the kit can be stored under normal refrigeration for a long period of time.

ASSAY PROCEDURE

The assay procedure is straightforward and easy to follow. Initially, the material to be assayed (the suspected toxicant) is dissolved in a suitable solvent and serially diluted in either a series of test tubes or alternatively in the wells of a microtitration plate.

Lyophilized bacteria, which have been resuspended in a medium containing growth nutrient and an agent to induce synthesis of beta-galactosidase, are added to the sample solutions to be assayed and incubated for 30-60 minutes. During this incubation period the bacteria are subjected to stess, relieved from the stress and stimulated to produce the enzyme beta-galactosidase. The user is, of course, unaware of all these processes, which occur automatically and sequentially.

When the incubation period is over, the test is terminated by the addition of the chromogenic solution. At those concentrations of tested material (s), which are toxic to the bacteria, no or little color development will occur. Strong color development, equal to that developed by untreated bacteria, indicates that little or no toxic activity occurred.

The media and buffers which may be employed in the practice of this invention and methods for employing them are described in the following examples.

EXAMPLE 1

Media and Buffers

Lyophilization Medium

| | |
|---|---|
| Trehalose | 0.5 M |
| Magnesium chloride | 0.004 M |
| Sodium chloride | 0.7% |
| MOPS (3-[N—morpholino]propanesulfonic acid) | 0.02 M |

L-Medium

| | |
|---|---|
| Bacto tryptone | 1% |
| Bacto yeast extract | 0.5% |
| Sodium chloride | 1% |

G-Medium

| | |
|---|---|
| Sodium chloride | 2% |
| Potassium chloride | 0.05 M |
| L-Glutamic acid mono sodium salt | 0.03% |
| IPTG | 0.0005 M |
| Sodium phosphate buffer | 0.02 M |

HM Medium

| | |
|---|---|
| Sodium dodecyl sulfate | 0.1% |
| $MgSO_4.7H_2O$ | 0.025% |
| beta-Mercaptoethanol | 0.27% |
| O—Nitro-Phenyl beta-D-galactoside | 1.2% |
| Tris HCl pH 9.0 | 0.2 M |

EXAMPLE 2

Lyophilization of Bacteria

*E. coli* ESS (Kohska et al., Biochem. Biophys. Res. Comm., Ibid) cells are grown in L-medium at 37° C. until the turbidity of the culture suspension reaches an optical density (O.D.) of 0.4 at 600 nm. The culture is centrifuged (4°, 10,000×g, 10 min.) and resuspended in lyophilization medium to an O.D. of 2.4 at 600 nm. 2 ml of the suspension is introduced into 12 ml glass serum vials (24×45 mm) and frozen in liquid nitrogen. Lyophilization is conducted in Labconco Freeze Dryer 8 and completed in 24 hours.

The media described in Example 1 and the lyophilized bacterial culture produced as in Example 2, may be packaged in kit form e.g., in separate containers.

EXAMPLE 3

Plasmolysis system (P-system)

A. Toxicant dilution

The test is performed in disposable microtitration plates, each containing 96 wells (12 wells in each of 8 rows) of approximately 0.3 ml total well volume. Such plates are commercially available from various manufacturers and suppliers of medical and scientific equipment (e.g., DYNATECH, FLOW, AMERICAN SCIENTIFIC PRODUCTS, THOMAS SCIENTIFIC, FISHER etc.). To each well 100 microliters of G-medium are added except for the first well of each row to which 200 microliters are added. The suspected toxicant is added in a volume of not more than 20 microliters to the first well in the row, containing the 200 liters of diluent. One hundred microliters are then taken from the first well and transferred to the second well (containing 100 microliters of diluent). Thus, a 1:1 dilution is obtained. After mixing, 100 microliters of the diluted material is taken and transferred to the next well in the row, constituting a further 1:1 dilution. The process is continued until the one well before the end of the row of wells, obtaining 10 two-fold dilutions (up to 1:2048) of the solution of the first well. The last well is the reaction blank free of toxicant. In each microtitration plate 8 different materials and their two-fold dilutions can be tested.

B. Bacterial Preparation

The lyophilized bacteria are rehydrated by 10 ml cold L-medium and incubated for 2 hours at B 37° C. Ten microliters of the incubated cells are added to each well of the microtitration plate, containing the suspect material(s) and their dilutions. The plate is incubated without shaking at 37° C. for 45 min.

C. Color Development

To each well, 100 microliters of HM medium (Example 1) are added and color development is determined by a microtitration plate reader (photometer) 10 minutes afterwards. HM medium will yield yellow color after development. Alternatively, O-nitro-phenyl-beta-D-galactoside, which develops a yellow color, and bromochloro-indoxyl-beta-D-galactoside (X-Gal), which develops a deep blue color, may be used. Solutions of the latter two chromogens are commercially available from Orgenics Ltd., POB 360, Yavne 70650, Israel, as components E and F of SOS CHROMOTEST kit, and are used as above. The selection of the chromogen substrate is based, of course, on the induced enzyme.

EXAMPLE 4

Lyophilization system (L-system)

Lyophilization is performed as with the P-system with the following changes:

A. Toxicant dilution is done in L-medium containing 0.5 mM IPTG.

B. Rehydrated bacteria are used immediately after rehydration without pre-incubation and incubated for 2 hours in the mixture.

EXAMPLE 5

Assaying the Toxicity of Sodium Azide

A solution of 10% sodium azide in water is prepared. Twenty microliters of sodium azide solution are added to the first well of a microtitration plate containing 200 microliter L-medium with 5 mM IPTG. Serial dilutions are performed to give final concentrations in the range of 10 mg/ml—0.0095 mg/ml. 15 microliters of bacterial suspension are added to every well and the plate is incubated for 2 hours as described in Example 4. To compare the efficiency of the HM and the Orgenics yellow chromogen solution in determining enzyme activity, the contents of each well (100 microliters) is divided into equal portions. To each, duplicate 50 microliters portions of one of the two chromogen solutions are added. A yellow color is developed and determined after 10 minutes.

| | OPTICAL DENSITY IN | |
|---|---|---|
| MG/ML AZIDE | HM | ORGENICS |
| 10 | 0.03 | 0.02 |
| 5 | 0.04 | 0.03 |
| 2.5 | 0.1 | 0.09 |
| 1.25 | 0.80 | 0.75 |
| 0.625 | 0.165 | 0.157 |
| 0.312 | 0.262 | 0.251 |
| 0.155 | 0.408 | 0.388 |
| 0.077 | 0.520 | 0.472 |
| 0.0385 | 0.752 | 0.642 |
| 0.019 | 1.00 | 0.90 |
| 0.0098 | 1.200 | 1.15 |
| 0 | 1.2 | 1.1 |

EXAMPLE 6

Toxicants and antibiotics tested in the L or P systems as described in Examples 3 and 4

| Toxicants | Solvent | Minimal inhibitory concentration (ug/ml) | System |
| --- | --- | --- | --- |
| Patulin | water | 0.5 | P |
| Mycotoxin T-2 | ethanol | 0.2 | P |
| Mycotoxin O.A.S. | ethanol | 0.6 | P |
| Na arsenite | water | 0.08 | P,L |
| Malathion | water | 25 | P,L |
| Simbush | ethanol | 10 | P,L |
| Sodium fluoroacetate | ethanol | 50 | P,L |
| Endosulfan | water | 12 | P |
| Endosulfan | water | 6.8 | L |
| NaN$_3$ | water | 19 | P,L |
| Simazine | water | 19 | P,L |
| Cacodylic acid | water | 750 | P,L |
| Halowax | ethanol | 19 | P,L |
| *Antibiotics* | | | |
| Penicillin G | methanol | 5 | P |
| Neomycin | ethanol | 5 | P |
| Ampicillin | water | 0.5 | P |
| Chloramphenicol | ethanol | 0.2 | P |
| Erythromycin | water | 0.1 | P |
| Rifampycin | water | 0.4 | P |

As may be seen above, the toxicity assay according to the invention allows for clear determination of minimum inhibitory concentration quickly for a wide variety of toxicants under field conditions.

The specification makes continual reference to "toxicants" and "antibiotics" as being the materials which are assayed according to the invention. However, it is to be understood that these terms are utilized for purposes of convenience only, and are not intended to be limiting. Thus, these terms have been used as shorthand designations for any substances which one desires to assay, which are capable of detection based upon the principle of de novo biomolecular synthesis inhibition.

Also, although the invention has been described with reference to a particular test microorganism, and specific enzyme inducers, it is to be understood that the invention is not limited to any particular test microorganism, and is quite obviously suitable to any test microorganism capable of responding to stress, stress recovery, and inducement in the manner described above.

Finally, although the invention has been specifically described with reference to particular means and embodiments, it is to be understood that the invention is not limited to the particulars disclosed and extends to all equivalents within the scope of the claims.

I claim:

1. A method for assaying an unknown specimen for the presence of a substance capable of inhibiting de novo synthesis of a biomolecule in a test microorganism, which comprises:
   (a) exposing a cell wall permeability-enhanced test micro-organism exhibiting delayed de novo synthesis of said biomolecule to said specimen, and assaying the extent of inhibition of synthesis of said biomolecule in said microorganism which inhibition results from the presence of said substance;
   wherein said micro-organism is a bacterium infected with a bacteriophage and wherein de novo biomolecule synthesis is inhibited by inhibiting phage expression in said infected micro-organism.

2. The method as defined by claim 1 wherein said substance capable of inhibiting de novo biomolecular synthesis is selected from the group consisting of toxicants and antibiotics.

3. The method as defined by claim 1, wherein said bacteriophage is Charon 4, containing a gene for beta-galactosidase.

4. The method as defined by claim 1 wherein said substance capable of inhibiting de novo biomolecular synthesis affects only the cell wall permeability of said micro-organism, and said method further comprises adding an auxiliary toxicant whose toxicity is limited by its inability to penetrate the cell wall of said micro-organism in an amount effective to (a) increase sensitivity to toxicants or (b) allow for the assay of substances which only affect cell wall permeability.

5. A method as defined by claim 1 wherein said substance is a toxicant.

6. A method of assaying for the presence of toxicants or antibiotics in a specimen, which comprises:
   (a) admixing said specimen with a stressed polysaccharide-deficient strain of *Escherichia coli* and a mixture comprising a specific inducer for an enzyme produced by said *E. coli;*
   (b) incubating the *E. coli* in the mixture;
   (c) adding a chromogenic substrate for said enzyme to said mixture; and
   (d) assaying the extent of the color change as an indication of the presence of said toxicant or antibiotic;
   wherein said mixture contains at least one factor promoting the recovery of said *E. coli* from the stress, said factor comprising potassium chloride and at least one member selected from the group consisting of proline and monosodium glutamate.

7. The method as defined by claim 6, wherein said enzyme is a beta-galactosidase and said specific inducer is a specific inducer for beta-galactosidase, wherein said specific inducer for beta-galactosidase is selected from the group consisting of isopropyl-beta-D-thiogalactopyranoside and lactose.

8. The method as defined by claim 6 wherein said mixture of said specific inducer comprises (a) isopropyl-beta-D-galactopyranoside, (b) sodium chloride in a concentration sufficient to stress said strain, and (c) potassium chloride and monosodium glutamate in amounts sufficient to enable recovery of said stressed *E. coli* from the stress.

9. The method as defined by claim 8 wherein said mixture further comprises a growth medium for said *E. coli.*

10. The method as defined by claim 6 wherein said specific inducer is a bacteriophage.

11. The method as defined by claim 6 further comprising adding an auxiliary toxicant to said mixture.

12. A kit for use in assaying the presence of a substance capable of inhibiting de novo biomolecular synthesis in a specimen, which comprises a separately contained combination of:
   (a) a stressed test micro-organism exhibiting increased cell wall permeability and delayed de novo protein synthesis;
   (b) at least one substance enabling the recovery from stress of said stressed test micro-organism, wherein said substance for enabling recovery from stress includes potassium chloride and a member selected from the group consisting of proline and monosodium glutamate;

(c) an indicator for indicating that de novo biomolecular synthesis has occurred; and (d) a specific inducer for beta-galactosidase selected from the group consisting of beta-D-thiogalactopyranoside and lactose.

13. A mixture comprising a recovering stressed polysaccharide-deficient strain of *E. coli* exhibiting increased cell wall permeability and delayed de novo protein synthesis and a specific inducer for inducing the production in said strain of an enzyme having a chromogenic substrate, said mixture further comprising at least one factor for promoting the recovery of said *E. coli* from stress, wherein said specific inducer for said enzyme is selected from the group consisting of isopropyl-beta-D-thiogalactopyranoside and lactose, wherein said at least one factor for promoting recovery of *E. coli* from stress comprises potassium chloride and a member selected from the group consisting of proline and monosodium glutamate.

14. The mixture as defined by claim 13 further comprising a specimen being assayed for the presence of a substance capable of inhibiting de novo biomolecular synthesis.

* * * * *